US009410175B2

(12) United States Patent
Gaudin et al.

(10) Patent No.: US 9,410,175 B2
(45) Date of Patent: Aug. 9, 2016

(54) PROCESS FOR MICROBIAL PRODUCTION OF A VALUABLE COMPOUND

(75) Inventors: Philippe Thierry François Gaudin, Den Hoorn (NL); Rogier Meulenberg, Delft (NL)

(73) Assignee: DSM IP ASSETS B.V., Heerlen (NL)

( * ) Notice: Subject to any disclaimer, the term of this patent is extended or adjusted under 35 U.S.C. 154(b) by 1312 days.

(21) Appl. No.: 11/886,582

(22) PCT Filed: Mar. 23, 2006

(86) PCT No.: PCT/EP2006/060996
§ 371 (c)(1),
(2), (4) Date: Jan. 25, 2008

(87) PCT Pub. No.: WO2006/100292
PCT Pub. Date: Sep. 28, 2006

(65) Prior Publication Data
US 2009/0017515 A1 Jan. 15, 2009

(30) Foreign Application Priority Data

Mar. 24, 2005 (EP) ..................................... 05102387

(51) Int. Cl.
*C12P 21/00* (2006.01)
*C12N 9/16* (2006.01)
*C12C 5/00* (2006.01)
*A23K 1/165* (2006.01)
*C12N 15/80* (2006.01)
*C12P 19/14* (2006.01)
*C07K 14/37* (2006.01)
*C12R 1/685* (2006.01)
*C07K 14/38* (2006.01)

(52) U.S. Cl.
CPC . *C12P 21/00* (2013.01); *C12N 9/16* (2013.01); *A23K 1/1653* (2013.01); *C07K 14/37* (2013.01); *C07K 14/38* (2013.01); *C12C 5/004* (2013.01); *C12N 15/80* (2013.01); *C12P 19/14* (2013.01); *C12R 1/685* (2013.01); *C12Y 301/03008* (2013.01); *C12Y 301/03026* (2013.01); *G01N 2333/914* (2013.01)

(58) Field of Classification Search
None
See application file for complete search history.

(56) References Cited

U.S. PATENT DOCUMENTS

| | | | |
|---|---|---|---|
| 3,105,015 A | 9/1963 | Tveit | |
| 4,927,751 A | 5/1990 | Memmert et al. | |
| 6,066,493 A * | 5/2000 | Shuster et al. | 435/254.3 |
| 6,433,152 B1 | 8/2002 | Lang et al. | |

FOREIGN PATENT DOCUMENTS

| | | |
|---|---|---|
| CZ | 9601597 A3 * | 10/1997 |
| DE | 4012238 A1 | 1/1991 |
| EP | 0 400 300 | 12/1990 |
| EP | 0 911 416 A2 | 4/1999 |
| GB | 1 545 766 | 5/1979 |
| RU | 1 419 152 | 7/1995 |
| RU | 1419152 C * | 7/1995 |
| WO | WO 90/00199 | 1/1990 |
| WO | WO 99/24448 | 10/1998 |
| WO | WO 9846772 A2 * | 10/1998 |
| WO | WO 2004/087934 | 10/2004 |
| WO | WO 2006/025735 | 3/2006 |

OTHER PUBLICATIONS

Mayer et al "Efficient Phytase Production by Hansenula polymorpha" Biotechnology and Bioengineering, May 5, 1999, 63(3), pp. 373-381.*
Zobač, P. et al. "The Effect of Microbial Phytase Applied in Feed Mixtures on Phosphorus and Calcium Utilization in Chicken Broilers" Živočí šná Výroba 1997, 41(1), pp. 13-22.*
Hall LA; Denning DW "Oxygen Requirements of *Aspergillus* Species" J Med Microbiol., Nov. 1994,41(5),pp. 311-315.*
P. Vats; D.K. Sahoo; U.C. Banerjee "Production of Phytase (myo-Inositolhexakisphosphate Phosphohydrolase) by Aspergillus niger van Teighem in Laboratory-Scale Fermenter" Biotechnol. Prog., 2004 (published online Jan. 20, 2004), 20(3), pp. 737-743.*
Gibbs et al "Growth of Filamentous Fungi in Submerged Culture: Problems and Possible Solutions" Critical Reviews in Biotechnology, 2000, 20(1):17-48.*
Koutinas, A.A. et al "Kinetic parameters of *Aspergillus awamori* in submerged cultivations on whole wheat flour under oxygen limiting conditions" Biochem. Eng. J., Oct. 2003 (pubilshed online Aug. 22, 2003) , 16(1), pp. 23-34 (doi:10.1016/S1369-703X(03)00018-4).*
Database EPODOC European Patent Office, The Hague, NL; Oct. 15, 1997, XP002342616 & CZ 9 601 597 A3, Oct. 15, 1997, 1 page.
Anonymous: "Biotechnical Pilot Plant" BTH Report 1996—Laboratory 115, Nov. 18, 1997, pp. 1-4, XP002342617.
International Search Report mailed Aug. 4, 2006 in PCT/EP2006/060996, 4 pages.
Written Opinion mailed Aug. 4, 2006 in PCT/EP2006/060996, 6 pages.
Wang et al, "Effects of process parameters on heterologous protein production in *Aspergillus niger* fermentation", J. Chem. Technol, Biotechnol. 78:1259-1266 (2003).

(Continued)

*Primary Examiner* — Louise W Humphrey
*Assistant Examiner* — Aaron J Kosar
(74) *Attorney, Agent, or Firm* — Nixon & Vanderhye P.C.

(57) ABSTRACT

The present invention relates to a process for the production of a valuable compound by cultivation of a microorganism comprising cultivating the microorganism in a medium wherein all nutrients are provided in excess over the whole cultivation period and wherein a suitable amount of oxygen is fed to the culture to maintain the culture under conditions of oxygen limitation.

6 Claims, 4 Drawing Sheets

(56) References Cited

OTHER PUBLICATIONS

Casas Lopez et al, "Fermentation optimization for the production of lovastatin by *Aspergillus terreus*: use of response surface methodology", J. Chem. Technol. Biotechnol. 79:1119-1126 (2004).

Kumar et al, "Repeated fed-batch process for improving lovastatin production", Process Biochemistry 36:363-368 (2000).

Yoo et al, "The Effect of Dissolved Oxygen on Microbial Transglutaminase Production by *Streptoverticillium morbaraense*", Korean J. Biotechnol. Bioeng. 18(2):155-160 (2003).

* cited by examiner

PROCESS FOR MICROBIAL PRODUCTION OF A VALUABLE COMPOUND

This application is the US national phase of international application PCT/EP2006/060996 filed 23 Mar. 2006 which designated the U.S. and claims benefit of EP 05102387.7, dated 24 Mar. 2005, the entire content of which is hereby incorporated by reference.

FIELD OF THE INVENTION

The present invention relates to the field of production of a valuable compound, preferably a protein, or a secondary metabolite or biomass as such, by microbial cultivation.

BACKGROUND OF THE INVENTION

The cultivation of microorganisms for the production of a valuable compound typically may be done under conditions wherein at least one nutrient is supplied to the culture in amounts resulting in growth limitation, especially in the production phase of the cultivation process. Typically, the nutrient limitation results in limitation of nitrogen carbon, or both for the microorganism cultivated.

Due to the growing industrial importance to produce proteins and other valuable compounds to one end, and to the poor yield of biomass formed per consumed gram sugar or mole oxygen to the other end, there is still a need to obtain an improved process for production of proteins and other valuable compounds in microorganisms. The present invention provides an improved method to produce proteins and other valuable compounds with high efficiency.

DESCRIPTION OF THE INVENTION

Figure 1:
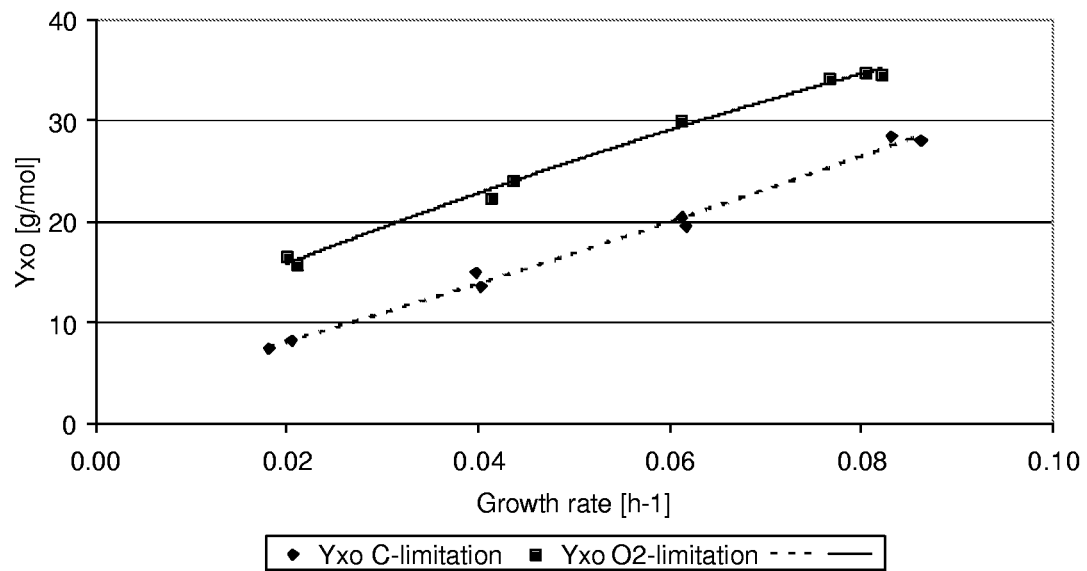
FIG. 1: yield of biomass on consumed oxygen (Yxo), vs. specific growth rate

In a first aspect, the present invention provides a process for the production of a valuable compound by cultivation of a microorganism comprising cultivating the microorganism in a medium wherein all nutrients are provided in excess over the whole cultivation period and feeding a suitable amount of oxygen to the culture to maintain the culture under conditions of oxygen limitation.

The composition of the nutrient medium that is used for cultivation of the microorganism is not critical to the invention, provided that all nutrients are supplied in excess during the whole cultivation period.

With the feature "supplied in excess" is meant that all the nutrients are supplied in a sufficient amount to avoid the establishment of a limitation in the growth of the microorganism. In this context, the nutrients may be supplied in batch only, i.e. supplied to the starting medium only, or may additionally be fed to the culture during the cultivation process. Preferably, one or more nutrients are fed to the culture next to supplying to the starting medium. More preferably, the nutrients that are fed are at least the carbon and/or the nitrogen source. Obviously, the nutrients should not be supplied in such an amount as to cause inhibitory or toxic effects.

According to the invention, a suitable amount of oxygen is fed to the culture to maintain the culture under conditions of oxygen limitation. A "suitable amount of oxygen" is herein defined as the amount of oxygen fed to the culture that effectuates a condition of oxygen limitation during cultivation.

In the context of the invention, the OTR (oxygen transfer rate) is the rate with which the oxygen is transferred from the gas phase to the liquid phase (culture broth). OTR is expressed as oxygen quantity per unit of time (e.g. moles/h). The OTR is conveniently determined from the difference between the amount of oxygen entering the fermentor and the amount of oxygen measured in the gas outlet.

Usually, oxygen will be fed as air. However, it is also possible to feed pure oxygen to the culture broth and/or air enriched with oxygen and/or air and oxygen in separate feeds.

In the context of the invention, the OUR (oxygen uptake rate) is the rate with which the microorganism consumes oxygen fed to the culture broth.

To maintain the broth under oxygen limitation according to the invention, the amount of oxygen fed to the culture broth should not exceed the amount of oxygen that is consumed by the microorganism. In other words, the OTR should be substantially identical to the OUR. "Substantially identical" means that the OTR is identical to the OUR with a deviation of preferably plus or minus 10%, more preferably 5%. Preferably, a suitable amount of oxygen is fed to the culture to further ensure that the OTR is as high as possible, i.e. as allowed by e.g. the fermentor configuration and/or the oxygen concentration in the gas feed, provided that the microorganism is able to immediately consume the oxygen. However, it will be clear to the skilled person that it is also possible to perform the cultivation process under oxygen limitation at an OTR that is lower than the maximum OTR that can be reached, for instance at 80 or 90% of the maximum OTR value.

When the OTR is substantially identical to the OUR, the dissolved oxygen concentration in the culture broth typically will be constant, and if oxygen limitation is controlling the cultivation, the dissolved oxygen will be zero or close to zero.

A preferred way to determine whether oxygen limitation exists in the cultivation process according to the invention is to determine the effect of an increase in nutrients feed on OTR. If the increase in nutrients feed is not accompanied by an increase in OTR, oxygen limitation exists. A most preferred way to determine whether oxygen limitation exists in the cultivation process according to the invention is to test the effect on OTR of, for instance, a slight decrease of the stirrer speed (e.g. 5%). If the OTR also decreases, then an oxygen limitation exists. If the OTR does not decrease and/or only the dissolved oxygen concentration decreases, oxygen limitation does not exist.

Measures that can be taken to modulate the OTR are commonly known to the skilled person. Preferably, conditions of modulated oxygen transfer rate (OTR) are established by modulation of at least one of the following parameters selected from the group consisting of: increasing agitation, increasing aeration, increasing overpressure, increasing oxygen percentage in the entering gas flow (oxygen enrichment), decreasing the broth weight, decreasing the overall broth viscosity. To modulate overall broth viscosity, measures can be taken related to medium composition, medium dilution, temperature alteration, cyclic pulse-pause feeding of nutrients (e.g. carbohydrates according to WO 03/029439). Preferably, the overall broth viscosity is modulated by altering the temperature of the broth to a level between 2 to 6 degrees Celsius above or below the level where optimal growth occurs. More preferably, the overall broth viscosity is decreased by increasing the temperature of the broth to a level between 2 to 6 degrees Celsius above the level where optimal growth occurs, in particular for filamentous fungi like *Aspergillus niger*. Of course, the opposite measures may be taken to decrease oxygen transfer if necessary. In this case, the overall broth viscosity is increased by decreasing the temperature of the broth to a level between 2 to 6 degrees Celsius below the level where optimal growth occurs.

In one embodiment of the invention, the microbial culture is maintained under oxygen limitation by regularly measuring the OTR, for instance each 1 or 2 hour(s), and modulating the OTR (e.g. by modulating the stirrer speed) dependent on the measured OTR relative to the OUR set point.

The OUR set point will depend on the microorganism that is cultured and the cultivation configuration, typically comprising e.g. the type of cultivation vessel, stirrer configuration, type of culture medium and nutrient feeding conditions. The OUR set point for a particular cultivation process therefore is established empirically by determining the OUR value that accompanies an OTR that is as high as possible, provided that the transferred oxygen is immediately consumed by the microorganism.

The maintenance of the culture under conditions of oxygen limitation may be done over the whole cultivation period. Preferably, the culture is maintained under conditions of oxygen limitation during the production phase. In this case, the condition of oxygen limitation is established and maintained after sufficient growth of the microorganism has occurred. It is clear to the skilled person that a minimum density of biomass is a prerequisite for oxygen limitation to occur, i.e. oxygen limitation is established after sufficient growth. In other words, the condition of oxygen limitation preferably is established and maintained in the production phase of the cultivation process, i.e. in the phase of production of the valuable compound. Typically, a microbial cultivation process may be divided in a growth phase directed to formation of biomass and a production phase directed to production of a valuable compound. The skilled person will comprehend that the two phases of cultivation may not be strictly separated in time, but may overlap to some extent. Moreover, the skilled person will comprehend that during any phase of the cultivation of the microorganism, the valuable compound will be produced to some extend.

The cultivation medium necessary for performing the cultivation process according to the invention is not critical to the invention. Nutrients are added to the process according to the needs of the organism in question, provided that the nutrients are supplied in excess. In the context of the invention, the nutrient is not oxygen.

The cultivation medium conveniently contains a carbon source, a nitrogen source as well as additional compounds required for growth of the microorganism and/or the formation of the valuable compound. For instance, additional compounds may be necessary for inducing the production of the valuable compound.

Examples of suitable carbon sources known in the art include glucose, maltose, maltodextrins, sucrose, hydrolysed starch, starch, molasses, oils. Examples of nitrogen sources known in the art include soy bean meal, corn steep liquor, yeast extract, ammonia, ammonium salts, nitrate salts, urea. Examples of additional compounds include phosphate, sulphate, trace elements and/or vitamins.

The total amount of carbon and nitrogen source to be added to the cultivation process according to the invention may vary depending on e.g. the needs of the microorganism and/or the length of the cultivation process.

The ratio between carbon and nitrogen source in a cultivation process may vary considerably, whereby one determinant for an optimal ratio between carbon and nitrogen source is the elemental composition of the product to be formed.

Additional compounds required for growth of a microorganism and/or for product formation, like phosphate, sulphate or trace elements, may be added h amounts that may vary between different classes of microorganisms, i.e. between fungi, yeasts and bacteria. In addition, the amount of additional compound to be added may be determined by the type of valuable compound that is formed.

Typically, the amount of medium components necessary for growth of a microorganism may be determined in relation to the amount of carbon source used in the cultivation, since the amount of biomass formed will be primarily determined by the amount of carbon source used.

The cultivation process according to the invention is preferably performed on an industrial scale. An industrial scale process is understood to encompass a cultivation process on a fermentor volume scale which is ≥0.01 m$^3$, preferably ≥0.1 m$^3$, preferably ≥0.5 m$^3$, preferably ≥5 m$^3$, preferably ≥10 m$^3$, more preferably ≥25 m$^3$, more preferably ≥50 m$^3$, more preferably ≥100 m$^3$, most preferably ≥200 m$^3$.

Any microorganism that produces a valuable compound or that is to be used as such as biomass may be subjected to the cultivation process according to the invention, e.g. bacterial, yeast and fungal organisms. For instance, microbial strains which are suitable for cultivation according to the invention include fungal strains, such as *Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Piromyces, Schizophyllum, Talaromyces, Thermoascus, Thielavia, Tolypocladium,* and *Trichoderma* strains, yeast strains, such as *Saccharomyces, Pichia, Phaffia* or *Kluyveromyces* strains and bacterial strains, such as *Bacillus, Escherichia* or *Actinomycete* strains. Especially filamentous organisms will benefit from the application of oxygen limitation to the cultivation process according to the invention. Filamentous organisms can be filamentous bacteria, like *Actinomycetes*, preferably *Streptomyces*, or can be filamentous fungi. Filamentous fungal strains include, but are not limited to, strains of *Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Piromyces, Schizophyllum, Talaromyces, Thermoascus, Thielavia, Tolypocladium,* and *Trichoderma*.

Preferred filamentous fungal cells belong to the genus of *Aspergillus* or *Trichoderma*, and more preferably a species of *Aspergillus niger, Aspergillus sojae, Aspergillus fumigatus, Aspergillus oryzae,* or *Trichoderma reesei*. A most preferred *Aspergillus niger* species is *Aspergillus niger* CBS513.88, and derivative thereof.

Several strains of filamentous fungi are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL) *Aspergillus niger* CBS 513.88, *Aspergillus oryzae* ATCC 20423, IFO 4177, ATCC 1011, ATCC 9576, ATCC14488-14491, ATCC 11601, ATCC12892, *Acremonium chrysogenum* ATCC 36225 or ATCC 48272, *Trichoderma reesei* ATCC 26921 or ATCC 56765 or ATCC 26921, *Aspergillus sojae* ATCC11906, *Chrysosporium lucknowense* ATCC44006 and derivatives thereof.

The microbial strain to be subjected to the process of the invention may be a naturally occurring microorganism, or a microbial strain derived from any suitable parent strain by any kind of mutagenesis technology, e.g. classical mutagenesis treatment or genetic engineering technology.

The valuable compound produced by the microorganism to be subjected to the process of the invention preferably is a polypeptide, e.g. an enzyme or a pharmaceutical protein. However, the process is also suitable for production of a metabolite, e.g. a carotenoid or vitamin, or for the production of biomass as such. The valuable compound may be encoded by a single gene or a series of genes composing a biosynthetic or metabolic pathway or may be the direct result of the product of a single gene or products of a series of genes. The valuable compound may be native to the microorganism or heterologous.

The term "heterologous compound" is defined herein as a compound which is not native to the cell; or a native compound in which structural modifications have been made to alter the native compound.

The valuable compound produced according to the invention may be a polypeptide. The polypeptide may be any polypeptide having a biological activity of interest. The term "polypeptide" is not meant herein to refer to a specific length of the encoded product and, therefore, encompasses peptides, oligopeptides, and proteins. The term "polypeptide" also encompasses two or more polypeptides combined to form the encoded product. Polypeptides also include hybrid polypeptides, which comprise a combination of partial or complete polypeptide sequences obtained from at least two different polypeptides wherein one or more may be heterologous to the filamentous fungal cell. Polypeptides further include naturally occurring allelic and engineered variations of the above-mentioned polypeptides and hybrid polypeptides. The polypeptide may be a collagen or gelatin, or a variant or hybrid thereof. The polypeptide may be an antibody or parts thereof, an antigen, a clotting factor, an enzyme, a hormone or a hormone variant, a receptor or parts thereof, a regulatory protein, a structural protein, a reporter, or a transport protein, protein involved in secretion process, protein involved in folding process, chaperone, peptide amino acid transporter, glycosylation factor, transcription factor, synthetic peptide or oligopeptide, intracellular protein. The intracellular protein may be an enzyme such as, a protease, ceramidases, epoxide hydrolase, aminopeptidase, acylases, aldolase, hydroxylase, aminopeptidase, lipase. The polypeptide may be an enzyme secreted extracellularly. Such enzymes may belong to the groups of oxidoreductase, transferase, hydrolase, lyase, isomerase, ligase, catalase, cellulase, chitinase, cutinase, deoxyribonuclease, dextranase, esterase. The enzyme may be a carbohydrase, e.g. cellulases such as endoglucanases, β-glucanases, cellobiohydrolases or β-glucosidases, hemicellulases or pectinolytic enzymes such as xylanases, xylosidases, mannanases, galactanases, galactosidases, pectin methyl esterases, pectin lyases, pectate lyases, endo polygalacturonases, exopolygalacturonases rhamnogalacturonases, arabanases, arabinofuranosidases, arabinoxylan hydrolases, galacturonases, lyases, or amylolytic enzymes; hydrolase, isomerase, or ligase, phosphatases such as phytases, esterases such as lipases, proteolytic enzymes, oxidoreductases such as oxidases, transferases, or isomerases. The enzyme may be a phytase. The enzyme may be an aminopeptidase, amylase, carbohydrase, carboxypeptidase, endo-protease, metalloprotease, serine-protease catalase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, proteolytic enzyme, invertase, laccase, lipase, mannosidase, mutanase, oxidase, pectinolytic enzyme, peroxidase, phospholipase, polyphenoloxidase, ribonuclease, transglutaminase, deaminase, asparaginase, glucose oxidase, hexose oxidase, monooxygenase.

The valuable compound produced according to the invention may be a polysaccharide. The polysaccharide may be any polysaccharide, including, but not limited to, a mucopolysaccharide (e.g., heparin and hyaluronic acid) and nitrogen-containing polysaccharide (e.g., chitin). In a more preferred option, the polysaccharide is hyaluronic acid.

The term "metabolite" encompasses both primary and secondary metabolites; the metabolite may be any metabolite. A preferred metabolite is citric acid.

The metabolite may be encoded by one or more genes, such as in a biosynthetic or metabolic pathway. Primary metabolites are products of primary or general metabolism of a cell, which are concerned with energy metabolism, growth, and structure. Secondary metabolites are products of secondary metabolism (see, for example, R. B. Herbert, The Biosynthesis of Secondary Metabolites, Chapman and Hall, New York, 1981).

The primary metabolite produced according to the invention may be, but is not limited to, an amino acid, fatty acid, nucleoside, nucleotide, sugar, triglyceride, or vitamin.

The secondary metabolite produced according to the invention may be, but is not limited to, an alkaloid, coumarin, flavonoid, polyketide, quinine, steroid, peptide, or terpene. The secondary metabolite may be an antifeedant, attractant, bacteriocide, fungicide, hormone, insecticide, or rodenticide.

A cultivation process according to the invention can be performed as a batch, a repeated batch, a fed-batch, a repeated fed-batch or a continuous cultivation process.

In a batch process, all medium components are added directly, as a whole, to the medium before the start of the cultivation process.

In a repeated batch process, a partial harvest of the broth accompanied by a partial supplementation of complete medium occurs, optionally repeated several times.

In a fed-batch process, part of the compounds necessary for microbial growth and/or product formation is supplied in the starting medium, prior to starting the cultivation process. In the course of the cultivation process, additional carbon source, nitrogen source and/or additional compounds as desired may be fed to the process, in one feed or in a separate feed for each compound.

In a repeated fed-batch or a continuous cultivation process, the complete starting medium is additionally fed during cultivation. The starting medium can be fed as a whole or in separate streams of e.g. carbon and nitrogen source. In a repeated fed-batch process, part of the cultivation broth comprising the biomass is removed at regular time intervals, whereas in a continuous process, the removal of part of the cultivation broth occurs continuously. The cultivation process is thereby replenished with a portion of fresh medium ensuring a constant volume and/or weight of the broth.

In a preferred embodiment of the invention, a fed-batch or repeated fed-batch process is applied, wherein the carbon source and/or the nitrogen source and/or additional compounds are fed to the cultivation process. In a more preferred embodiment, the carbon and/or nitrogen source are fed to the cultivation process.

A further aspect of the present invention concerns the option of downstream processing of the cultivation broth. The use of oxygen limitation according to the invention facilitates downstream processing, especially because of the high yield of the valuable compound and the low amount of by-products. Downstream processing may include recovery as well as formulation steps. Preferably, the valuable compound obtained by the oxygen limited process of the invention is recovered from the cultivation broth and/or is formulated in a suitable composition.

After the cultivation process is ended, the valuable product may be recovered from the cultivation broth, using standard technology developed for recovery of the valuable compound of interest. The relevant downstream processing technology to be applied thereby depends on the nature and cellular localization of the valuable compound and on the desired purity level of the product of interest. In a typical recovery process, the biomass is separated from the cultivation fluid using e.g. centrifugation or filtration. The valuable compound then is recovered from the biomass in the case that the valuable product is accumulated inside or is associated with the microbial cells. Of course, the biomass as such may also be used. Otherwise, when the valuable product is excreted from the microbial cell, it is recovered from the cultivation fluid. The biomass and/or valuable compound may be formulated as liquid or solid products. Preferably, the valuable compound obtained by the process of the invention is recovered from the cultivation broth and/or is formulated in a suitable composition.

The present invention is further illustrated by the following example, which should not be construed as limiting the scope of the invention.

EXAMPLES

Example 1

Industrial Production of Phytase by *Aspergillus niger*

*Aspergillus niger* CBS513.88 overexpressing phytase was designed and constructed according to WO 98/46772. Working cell banks were stored in vials of approximately 1 ml at −80° C.

Inoculation Procedure:

The content of one vial was added to a pre-culture medium: baffled 2 L-shake flask (20 g/L Corn Steep Solid, 20 g/L glucose, pH 6.5 (with NaOH), 300 mL medium, steam-sterilized 30 min. at 121° C.). Pre-culture was grown 40 h at 34° C. and 220 rpm. Timing can of course be adapted to the shake flask configuration and the vial viability.

Continuous Cultures:

The medium is composed of a mix of glucose and maltodextrins, as well as a salt fraction. The salt fraction was fitting with WO98/37179, Table 1, p. 12. Deviations from this table were: MgSO4.7aq 0.25 g/L, CaCl2.2aq 0.22 g/L, (NH4)2SO4 6 g/L, citric acid 0.1aq 0.2 g/L (chelating agent). The medium composition was identical for the batch and the feed. Glucose concentration was 22.5 or 45 g/L for carbon limitation or oxygen limitation, respectively, while maltodextrins were 2.5 or 5.0 g/L, respectively. The medium was steam-sterilized in two fractions, one of which combining sugars and calcium chloride. The pH of the medium salts fraction was 4.5 (sulfuric acid) before sterilization, and that same pH was controlled (sulfuric acid, ammonia) after having pooled the fractions in the fermentor. Temperature was controlled at 34° C. Airflow was 1.0 or 0.5 vvm (volume air per volume broth per minute) for carbon limitation or oxygen limitation, respectively. Bioreactors were inoculated at 6% inoculum ratio. Working volume was 10 L. For carbon-limited fermentation, DOT was controlled at 20% of the DOT of the broth before inoculation. The term "DOT" (Dissolved Oxygen Tension) is defined as a measure of dissolved oxygen and is expressed as a percentage of the dissolved oxygen at saturation with air at atmospheric pressure, i.e. 100% DOT is the maximum amount of oxygen to be dissolved at atmospheric pressure. Controlling fermentation by DOT is typical for carbon limited fermentations.

For oxygen-limited fermentation, the oxygen transfer rate was controlled (thanks to agitation speed) at 80% of the value measured under carbon limitation for the same dilution rate, establishing thus oxygen limitation. CLEROL (defoamer) was used as antifoam on a periodic manner: 2 sec. every 30 min. for the first 24 h, then 2 sec. every hour later on. To reach steady state, at least 5 volume changes were made. For every steady state a new fermentation was run.

Figure 2:
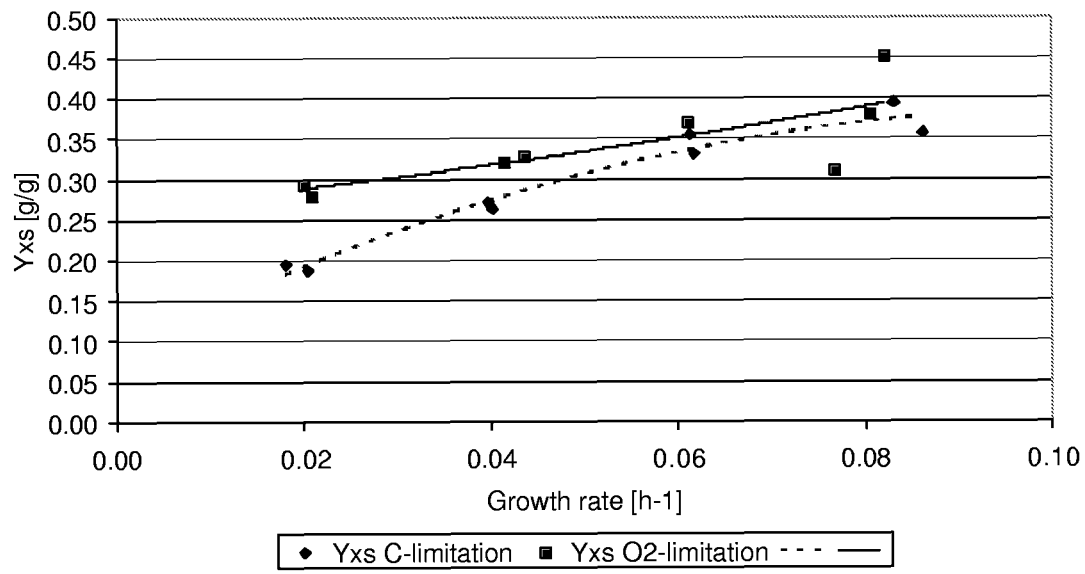
FIG. 2: yield of biomass on consumed sugar (Yxs), vs. specific growth rate.
Figure 3:
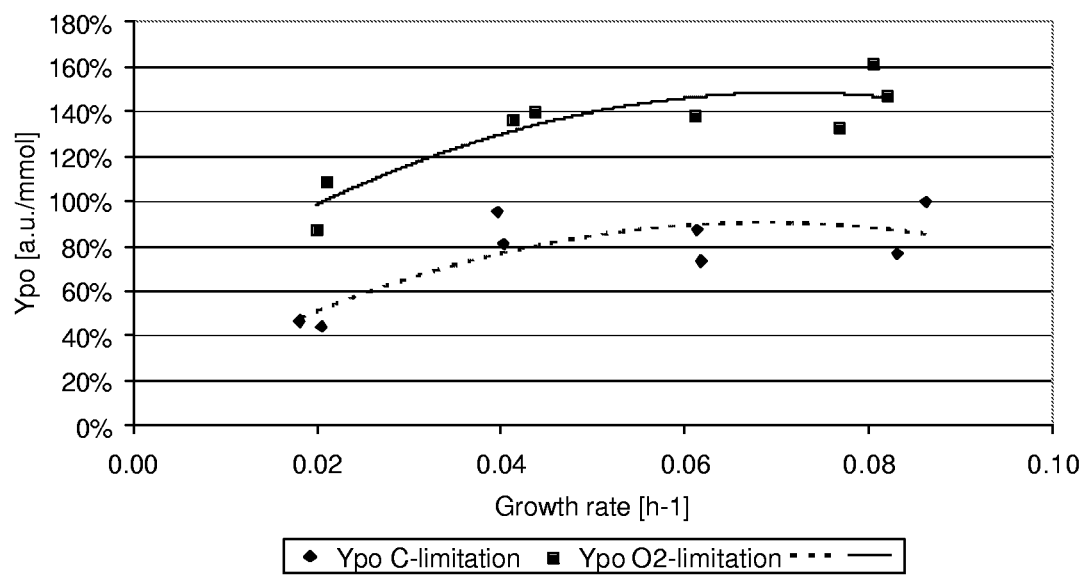
FIG. 3: yield of phytase on consumed oxygen (Ypo), arbitrary units, vs. specific growth rate.
Figure 4:
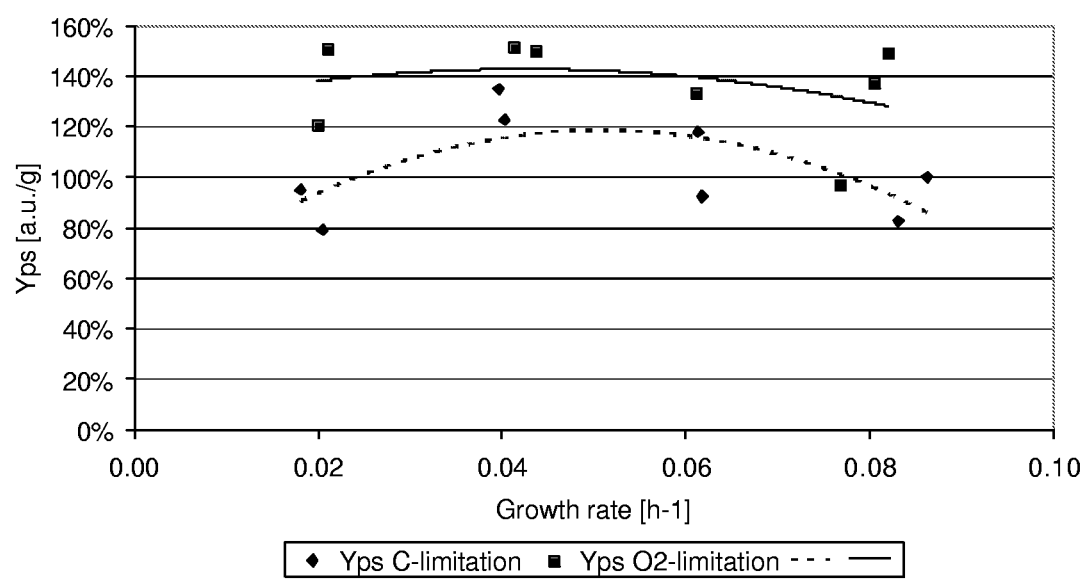
FIG. 4: yield of phytase on consumed sugar (Yps), arbitrary units, vs. specific growth rate.

Results:

As can be seen from FIG. 1 to FIG. 4 (each point in the graphs represents a separate steady state), oxygen limitation provides clearly higher biomass yields on glucose and on oxygen as compared to carbon limitation. More interestingly, the enzyme yields on glucose and on oxygen are also enhanced, despite a lower oxygen uptake rate. This clearly translates into a higher productivity and a more cost effective process when fermentation is run under oxygen limitation.

The invention claimed is:

1. A process for the increased production of an enzyme comprising:
   (a) cultivating a filamentous fungus belonging to the species *Aspergillus niger* in a culture broth in a cultivation process that comprises: i) a cultivating growth phase wherein filamentous fungal biomass is formed and ii) a cultivating production phase wherein the enzyme is produced by the filamentous fungal biomass, wherein said cultivating growth phase is conducted in the presence of all filamentous fungal nutrients in an amount sufficient to avoid the establishment of a nutrient limitation in the growth of the filamentous fungus, wherein the filamentous fungal nutrients comprise a carbon source, a nitrogen source as well as additional compounds required for growth of the filamentous fungus and/or the production of the enzyme, wherein said additional compounds comprise phosphate, sulfate, trace elements and/or vitamins and said cultivating production phase is conducted in the presence of all filamentous fungal nutrients except oxygen in an amount sufficient to avoid the establishment of a limitation of nutrients other than oxygen in the production phase, and wherein the cultivating production phase is conducted in the presence of an amount of oxygen suitable to establish and maintain conditions of oxygen limitation during the cultivating production phase, wherein the suitable amount of oxygen is fed to the culture broth during the cultivating production phase to ensure that the oxygen transfer rate (OTR) of the culture broth is identical to the oxygen uptake rate (OUR) of the culture broth with a deviation of plus or minus 10%, and wherein the suitable amount of oxygen is fed to the culture broth to further ensure that the OTR is as high as possible; and
   (b) recovering from the culture broth the enzyme obtained in the cultivating production phase, said enzyme yield obtained in the cultivating production phase being greater than obtainable by a similar process wherein said cultivating production phase is conducted under conditions such that all nutrients including oxygen are provided to the culture broth in an amount sufficient to avoid the establishment of a limitation of nutrients.

2. The process according to claim 1, wherein the OTR is modulated by modulating at least one parameter selected from the group consisting of: agitation of the culture broth, aeration of the culture broth, overpressure of the culture broth, oxygen percentage in the entering gas flow of the culture broth, weight of the culture broth, and overall viscosity of the culture broth.

3. The process according to claim 2, wherein the overall culture broth viscosity is modulated by altering the temperature of the culture broth to a level between 2 to 6 degrees Celsius above or below the level where optimal growth of the filamentous fungus occurs.

4. The process according to claim 3, wherein the overall culture broth viscosity is decreased by increasing the temperature of the culture broth to a level between 2 to 6 degrees Celsius above the level where optimal growth of the filamentous fungus occurs.

5. The process according to claim 3, wherein the overall culture broth viscosity is increased by decreasing the temperature of the culture broth to a level between 2 to 6 degrees Celsius below the level where optimal growth of the filamentous fungus occurs.

6. The process according to claim 1, wherein the enzyme obtained in step (b) is formulated in a liquid or solid product.

* * * * *